US005457239A

United States Patent [19]
Frank et al.

[11] Patent Number: 5,457,239
[45] Date of Patent: Oct. 10, 1995

[54] PROCESS FOR FORMYLATION OF AROMATIC COMPOUNDS

[75] Inventors: Walter C. Frank, Holland, Pa.; Richard L. Veazey, East Windsor; John J. Mahurter, Trenton, both of N.J.; Mark J. Jenkins, Atherton; Neil R. Fairfax, Lymm, both of England

[73] Assignee: Union Camp Corporation, Princeton, N.J.

[21] Appl. No.: 249,035

[22] Filed: May 25, 1994

[51] Int. Cl.$^6$ ............................ C07C 45/00; C07C 45/61
[52] U.S. Cl. .................. 568/433; 568/326; 568/328; 568/411; 568/426; 568/436; 568/437; 568/439; 568/440
[58] Field of Search .................... 568/426, 437, 568/439, 440, 326, 328, 433; 585/411, 459; 260/599

[56] References Cited

U.S. PATENT DOCUMENTS

| | | | |
|---|---|---|---|
| 2,800,511 | 7/1957 | Carpenter | 260/599 |
| 2,897,237 | 7/1959 | Carpenter | 260/592 |
| 3,246,044 | 4/1966 | Wood et al. | 260/668 |
| 3,369,048 | 2/1968 | Hamilton et al. | 260/599 |
| 3,379,785 | 4/1968 | Kahn | 260/668 |
| 3,856,875 | 12/1974 | Wood et al. | 260/668 |
| 4,195,040 | 3/1980 | Renner | 260/599 |
| 4,284,818 | 8/1981 | Sato et al. | 568/323 |
| 4,352,748 | 10/1982 | Traas et al. | 252/522 |
| 4,551,573 | 11/1985 | Cobb | 585/459 |
| 4,605,778 | 8/1986 | Willis et al. | 568/433 |
| 4,767,882 | 8/1988 | Suzukamo et al. | 560/100 |
| 4,877,910 | 10/1989 | Frank | 585/411 |
| 4,877,911 | 10/1989 | Frank | 585/411 |
| 4,877,912 | 10/1989 | Frank | 585/411 |
| 4,877,913 | 10/1989 | Frank | 585/411 |
| 4,877,914 | 10/1989 | Frank | 585/411 |
| 4,877,915 | 10/1989 | Frank | 585/411 |
| 4,877,916 | 10/1989 | Frank | 585/411 |
| 4,908,349 | 3/1990 | Gozenbach et al. | 512/26 |
| 5,087,785 | 2/1992 | Frank | 585/459 |
| 5,126,492 | 6/1992 | Milstein et al. | 568/437 |
| 5,162,588 | 11/1992 | Fehr | 568/328 |
| 5,169,974 | 12/1992 | Harris et al. | 568/414 |

FOREIGN PATENT DOCUMENTS

| | | |
|---|---|---|
| 0301375 | 2/1989 | European Pat. Off. . |
| 0393742 | 10/1990 | European Pat. Off. . |
| 57-40420 | of 1982 | Japan . |
| 603685 | 6/1948 | United Kingdom . |
| 1331664 | 9/1973 | United Kingdom . |

OTHER PUBLICATIONS

Oliver et al., *Synthesis*, "A Convenient Synthesis of a χ–Fluoro Carboxylic Acids", pp. 273–275 (1994).
Reeve et al., *Journal of the American Chemical Society*, "Reactions of Aryl (trichloromethyl) carbinols with Sulfur Nucleophiles . . . ", pp.–647–651 (1967).
Reeve et al., *Journal of Organic Chemistry*, "Reaction of Cyanamide with Aryl (trichloromethyl) carbinols. A Novel Synthesis . . . ", pp. 1005–1007 (1969).
Reeve et al., *JACS*, "The Synthesis of α–Methoxyarylacetic Acids from the Base–catalyzed Condensation . . . ", vol. 82, pp. 4062–4066 (1960).
Reeve et al., *Journal of Organic Chemistry*, "Preparation of Amino Acids from Trichloromethylcarbinols", vol. 29, pp. 1148–1150 (1964).
Olah et al.,*Chemical Reviews*, "Formylating Agents", vol. 87, No. 4, pp. 671–680 (1987).
Effenberger, *Angew. Chem. Int. Ed. Engl.*, "Electrophilic Reagents–Recent Developments and Their Preparative Application", vol. 19, No. 3, pp. 151–171 (1980).
Crounse, *Organic Reactions*, "The Gattermann–Koch Reaction", Ch. 6, pp. 290–300 (1949).,
Coleman et al., *Organic Syntheses*, "p–Tolualdehyde", vol. 2, pp. 583–587 (1943).
Martinez et al., *J. Chem. Soc. Chem. Commun.*, "A New Procedure for Formylation of Less Active Aromatics", pp. 1571–1572 (1990).
Rahm et al., *Synthetic Communications*, "Acetone Cyanohydrin, A Convenient Formylation Reagent for Arenes", vol. 12, No. 6, pp. 485–487 (1982).
Olah et al., *JACS*, "Formylation with Formyl Fluoride: A New Aldehyde Synthesis and Formylation Method", vol. 82, pp. 2380–2382 (1960).
Luknitskii, *Chemical Reviews*, "The Chemistry of Chloral", vol. 75, No. 3, pp. 259–289 (1975).
Reeve et al., *Canadian Journal of Chemistry*, "The Reaction of Chloral with Halobenzenes and with 2,4–Dichlorophenol", vol. 44, pp. 575–583 (1966).
Reeve et al., *Canadian J. of Chem.*, "Reaction of Chloral with Naphthalene, and the Synthesis of α–Methoxynaphthylacetic Acids from Naphthyl(trichloromethyl) Carbinols", vol. 46, pp. 2233–2237 (1968).
Ettel et al., *Collect Czech. Chem. Commun.*, "Préparation Des p–Chloro– ET p–Bromophényltrichhloréthyl–Carbinols et Certains de Leurs Dérivés", vol. 15, pp. 520–527 (1950).
Reimschneider, *Mb. Che. Bd.*, "Kondensationen mit halogenierten Aldehyden. VIII. Mitteilung: Borfluorid und Borfluorid–Eisessig als Kondensationsmittel", vol. 84, pp. 1228–1233 (1953).
Olszanowski et al., *Przem. Chem.*, "Studies on the Synthesis of Para–Substituted Phenyltrichloromethyl Carbinols", vol. 60, No. 1, pp. 33 . 35 (1981) (English language abstract).
karminski et al., *Zesz. Nauk. Politech.*, "Synthesis of 1,1, 1–trichloro–2–(p–isopropyl phenyl)–2–hydroxyethane", vol. 73, pp. 35–40 (1975) (English language abstract).
Riemschneider, *Monatsh*, "2,2, (List continued on next page.)

*Primary Examiner*—Werren B. Lone
*Attorney, Agent, or Firm*—Woodcock, Washburn, Kurtz, Mackiewicz & Norris

[57] ABSTRACT

A process for the preparation of a formylated aromatic compound comprising contacting an aromatic compound with (i) a halogenated compound in the presence of a Lewis acid, and (ii) a base, is described. The subject process provides an efficient and effective means of preparing formylated compounds which may be useful in a wide variety of applications.

54 Claims, No Drawings

OTHER PUBLICATIONS

2–trichloro–1–1(χ–aryl)ethyl χ–arylsylfonates", pp. 1008–1012 (1951) (English language abstract).

Riemschneider, *Monatsh*, "The Condensation of Mesitylene with Chloral", vol. 83, pp. 828–829 (1952) (English language abstract).

Frankforter et al., *JACS*, "The Action of Chloral, Chloral Hydrate, and Bromal on Certain Organic Compounds in the Presence of Aluminum Chloride", vol. 36, pp. 1511–1529 (1914).

Silva e Lins, et al., *J. Chem. Soc. Perkin Trans. II*, "Kinetics of the Decomposition of 1–Aryl–2,2,2–Trihalogenoethanols in Aqueous Base", pp. 1521–1526 (1984).

Menegheli et al., *Synthetic Communications*, vol. 17, No. 4, pp. 457–464 (1987).

Haller and Savariac, *Organic Chemistry*, "Research on a Method of Preparation of Cyclic Aldehydes", *C.R., 1908. 2nd se, ester (t. CXLVI, No. 6) (translation)*.

Ferraccioli et al., *Synthesis*, "General and Efficient Synthesis of 1,1,1–trichloro–2–alkanols", pp. 327–328 (1990).

Arnold and Rondestvedt, *JACS*, "Steric Effect of Methylene Groups", pp. 1265–1267 (Aug., 1945).

Chattaway et al., *J. Chem. Soc.*, pp. 701 and 703 (1934).

March, *Advanced Organic Chemistry*, "Reactions, Mechanisms, and Structure", pp. 540, 542–546, and 548–549 (1992).

Taylor, "Electrophilic Aromatic Substitution", pp. 244–245 and 254–255 (John Wiley & Sons, New York, N.Y. (1990).

Bedoukian, Paul Z., *Perfumery and Flavoring Synthetics*, 3rd ed., pp. 334–336, Allured Publishing Corporation, Wheation, Ill. (1986).

Fehr et al., *Helv. Chim. Acta*, vol. 72, pp. 1537–1553 (1989).

PROCESS FOR FORMYLATION OF AROMATIC COMPOUNDS

BACKGROUND OF THE INVENTION

Formylation is an important process in organic chemistry. The versatile chemical properties of formylated compounds and their usefulness in a variety of applications as end products and as intermediates, makes them a significant family of compounds. Accordingly, researchers have devoted a great deal of effort over the years to the development of effective formylation technology.

One of the earliest reported methodologies for the formylation of an aromatic compound is the well known Gattermann-Koch reaction, first described in 1897. In accordance with this reaction scheme, benzene and alkylbenzenes are reacted with carbon monoxide and hydrogen chloride in the presence of ammonium chloride at high pressure to produce formylated compounds. Addition of cuprous chloride allows the reaction to proceed at atmospheric pressure.

Hamilton et al., U.S. Pat. No. 3,369,048, seeking to improve on the Gattermann-Koch reaction, disclose a variation wherein crystalline aluminosilicate catalysts are employed in the reaction in lieu of aluminum chloride and cuprous chloride.

Renner, U.S. Pat. No. 4,195,040, provides still another variation of the Gatterman-Koch process wherein carbon monoxide, hydrogen chloride and an aluminum chloride catalyst are employed in the presence of a chlorobenzene solvent.

Rahm et al. *Synthetic Communications*, Vol. 12, No. 6, pp. 485–487 (1982) describes a process wherein aromatic compounds are formylated using acetone cyanohydrin and aluminum chloride.

Martinez et al., *J. Chem. Soc. Chem. Commun.*, pp. 1571–1572 (1990) provides a process for the formylation of less active aromatic compounds using a trifluoromethanesulphonic anhydride/dimethylformamide complex.

However, many of these, and other, prior art processes for the formylation of aromatic compounds suffer from disadvantages which make them commercially problematic and/or impractical. Indeed, many of the aromatic formylation methods developed to date employ difficult reaction schemes, require expensive equipment, necessitate the use of costly and/or hazardous reagents, and/or are applicable to only a select number of aromatic compounds.

New and/or better processes for the formylation of aromatic compounds are needed. The present invention meets this need by seeking to address many of the drawbacks of prior art processes. The present invention provides a new and surprisingly effective process which is useful for the formylation of a wide variety of aromatic compounds. The present process employs a relatively simple and economically feasible methodology, and provides a practical solution to many of the problems of formylation technology to date.

SUMMARY OF THE INVENTION

The present invention is directed to a novel process for the preparation of formylated aromatic compounds of the Formula [II]:

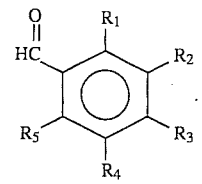

Specifically, in accordance with the subject invention, an aromatic compound of the Formula [I]

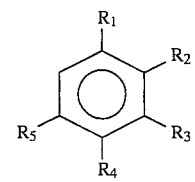

is contacted with a halogenated compound selected from the group consisting of

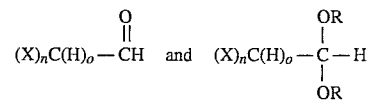

in the presence of a Lewis acid, followed by a base. In the above formulas:

X is Cl, F or Br;

each R is, independently, H, or a $C_1$–$C_{30}$ alkyl which may be substituted with no more than one of the following groups: hydroxy, methoxy, ether, nitrile or nitro;

n is 2 or 3;

o is 3–n;

$R_1$ is a $C_1$–$C_{30}$ alkyl, or a $C_1$–$C_{30}$ alkoxy;

$R_2$ is H, a $C_1$–$C_{30}$ alkyl, or a $C_1$–$C_{30}$ alkoxy;

or $R_1$ and $R_2$ are taken together to form a $C_3$–$C_4$ alkyl, which may be substituted with one or more $C_1$–$C_{30}$ alkyl groups;

$R_3$ is H, a $C_1$–$C_{30}$ alkyl, or a $C_1$–$C_{30}$ alkoxy;

or $R_2$ and $R_3$ are taken together to form a $C_3$–$C_4$ alkyl, which may be substituted with one or more $C_1$–$C_{30}$ alkyl groups;

$R_4$ is H, a $C_1$–$C_{30}$ alkyl, or a $C_1$–$C_{30}$ alkoxy;

or $R_3$ and $R_4$ are taken together to form a $C_3$–$C_4$ alkyl, which may be substituted with one or more $C_1$–$C_{30}$ alkyl groups; and $R_5$ is a $C_1$–$C_{30}$ alkyl, or a $C_1$–$C_{30}$ alkoxy;

or $R_4$ and $R_5$ are taken together to form a $C_3$–$C_4$ alkyl, which may be substituted with one or more $C_1$–$C_{30}$ alkyl groups;

provided that:

(i) when $R_3$ is H, then $R_2$ and $R_4$ must be other than H;

(ii) no more than one of $R_1$, $R_2$, $R_3$, $R_4$ and $R_5$ are a $C_1$–$C_{30}$ alkoxy;

(iii) no more than two of $R_1$ and $R_2$, $R_2$ and $R_3$, $R_3$ and $R_4$, or $R_4$ and $R_5$, taken together, are a $C_3$–$C_4$ alkyl;

(iv) when $R_1$ and $R_2$, taken together, are a $C_3$–$C_4$ alkyl, then $R_2$ and $R_3$, may not be taken together to form a $C_3$–$C_4$ alkyl;

(v) when $R_2$ and $R_3$, taken together, are a $C_3$–$C_4$ alkyl, then $R_3$ and $R_4$, may not be taken together to form a $C_3$–$C_4$ alkyl;

(vi) when $R_3$ and $R_4$, taken together, are a $C_3$–$C_4$ alkyl, then $R_4$ and $R_5$, may not be taken together to form a $C_3$–$C_4$ alkyl; and (vii) each $R_1$ and $R_2$, $R_2$ and $R_3$, $R_3$ and $R_4$, or $R_4$ and $R_5$ taken together to form a $C_4$ alkyl is substituted with no more than six $C_1$–$C_{30}$ alkyl groups.

The subject process provides an efficient and effective means of preparing formylated aromatic compounds which may be useful in a wide variety of applications. These and other aspects of the present invention are described in more detail below.

DETAILED DESCRIPTION OF THE INVENTION

The present invention is directed to a novel process for the preparation of formylated aromatic compounds comprising contacting an aromatic compound of Formula [I] with a halogenated compound in the presence of a Lewis acid, followed by a base, to yield an aromatic compound of Formula [II].

A wide variety of formylated compounds may be prepared in accordance with this process, including compounds of the Formula [II]:

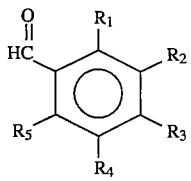

[II]

by subjecting a corresponding aromatic compound, such as a compound of the Formula [I]

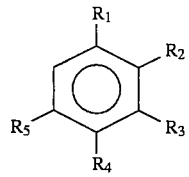

[I]

to the conditions of the present process, wherein, in the above formulas, $R_1$ through $R_5$ are defined as follows:

$R_1$ is a $C_1$–$C_{30}$ alkyl, or a $C_1$–$C_{30}$ alkoxy;

$R_2$ is H, a $C_1$–$C_{30}$ alkyl, or a $C_1$–$C_{30}$ alkoxy;

or $R_1$ and $R_2$ are taken together to form a $C_3$–$C_4$ alkyl, which may be, if desired, substituted with one or more $C_1$–$C_{30}$ alkyl groups;

$R_3$ is H, a $C_1$–$C_{30}$ alkyl, or a $C_1$–$C_{30}$ alkoxy;

or $R_2$ and $R_3$ are taken together to form a $C_3$–$C_4$ alkyl, which may be, if desired, substituted with one or more $C_1$–$C_{30}$ alkyl groups;

$R_4$ is H, a $C_1$–$C_{30}$ alkyl, or a $C_1$–$C_{30}$ alkoxy;

or $R_3$ and $R_4$ are taken together to form a $C_3$–$C_4$ alkyl, which may be, if desired, substituted with one or more $C_1$–$C_{30}$ alkyl groups; and $R_5$ is a $C_1$–$C_{30}$ alkyl, or a $C_1$–$C_{30}$ alkoxy;

or $R_4$ and $R_5$ are taken together to form a $C_3$–$C_4$ alkyl, which may be, if desired, substituted with one or more $C_1$–$C_{30}$ alkyl groups;

provided that:

(i) when $R_3$ is H, then $R_2$ and $R_4$ must be other than H;

(ii) no more than one of $R_1$, $R_2$, $R_3$, $R_4$ and $R_5$ are a $C_1$–$C_{30}$ alkoxy;

(iii) no more than two of $R_1$ and $R_2$, $R_2$ and $R_3$, $R_3$ and $R_4$, or $R_4$ and $R_5$, taken together, are a $C_3$–$C_4$ alkyl;

(iv) when $R_1$ and $R_2$, taken together, are a $C_3$–$C_4$ alkyl, then $R_2$ and $R_3$, may not be taken together to form a $C_3$–$C_4$ alkyl;

(v) when $R_2$ and $R_3$, taken together, are a $C_3$–$C_4$ alkyl, then $R_3$ and $R_4$, may not be taken together to form a $C_3$–$C_4$ alkyl;

(vi) when $R_3$ and $R_4$, taken together, are a $C_3$–$C_4$ alkyl, then $R_4$ and $R_5$, may not be taken together to form a $C_3$–$C_4$ alkyl; and (vii) each $R_1$ and $R_2$, $R_2$ and $R_3$, $R_3$ and $R_4$, or $R_4$ and $R_5$ taken together to form a $C_4$ alkyl is substituted with no more than six $C_1$–$C_{30}$ alkyl groups.

As used herein, unless the context requires otherwise, the term "alkyl" denotes a linear, branched, or cyclical hydrocarbon. Preferably, the alkyl is a linear or branched hydrocarbon, most preferably a linear hydrocarbon.

For reasons such as ease of synthesis and/or commercial usefulness of the end product, etc., the following classes of aromatic compounds within the scope of Formulas [I] and [II] are preferred.

As one preferred class, the Formula [I] and [II] compounds are preferably those wherein $R_1$ and $R_2$, taken together, are a $C_3$–$C_4$ alkyl which may be, if desired, substituted with one or more $C_1$–$C_{30}$ alkyl groups, such as the Formula [I] compounds

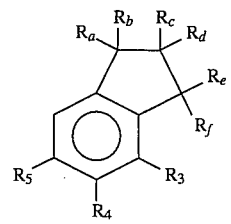

[Ia]

and

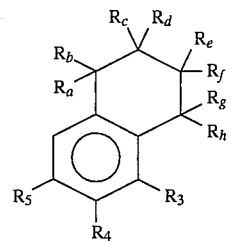

[Ib]

and the corresponding Formula [II] compounds

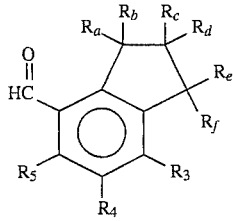

and

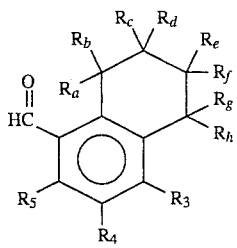

wherein: $R_3$, $R_4$ and $R_5$ are as previously defined, and wherein:

$R_a$, $R_b$, $R_c$, $R_d$, $R_e$, $R_f$, $R_g$ and $R_h$ are, independently, H or a $C_1$–$C_{30}$ alkyl group, provided that in Formulas [Ib] and [IIb], at least two of $R_a$, $R_b$, $R_c$, $R_d$, $R_e$, $R_f$, $R_g$ and $R_h$ are H (in other words, when $R_1$ and $R_2$ are taken together to form a $C_4$ alkyl, the $C_4$ alkyl is substituted with no more than six $C_1$–$C_{30}$ alkyl groups). Within the requirements of the above formulas, preferably $R_3$, $R_4$, $R_5$, $R_a$, $R_b$, $R_c$, $R_d$, $R_e$, $R_f$, $R_g$ and $R_h$, independently, is a $C_1$–$C_{10}$ alkyl group, more preferably a $C_1$–$C_3$ alkyl group, and most preferably $CH_3$.

As another preferred class, the Formula [I] and [II] compounds are preferably those wherein $R_2$ and $R_3$, taken together, are a $C_3$–$C_4$ alkyl which may be, if desired, substituted with one or more $C_1$–$C_{30}$ alkyl groups, such as the Formula [I] compounds

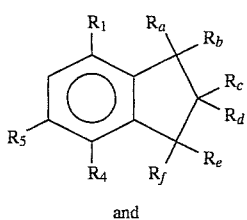

and

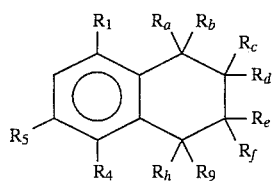

and the corresponding Formula [II] compounds

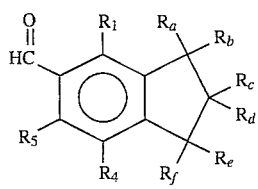

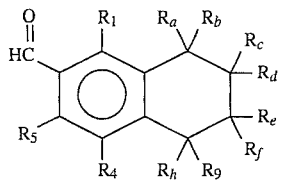

wherein: $R_1$, $R_4$ and $R_5$, are as previously defined, and wherein:

$R_a$, $R_b$, $R_c$, $R_d$, $R_e$, $R_f$, $R_g$ and $R_h$ are, independently, H or a $C_1$–$C_{30}$ alkyl group, provided that in Formulas [Id] and [IId], at least two of $R_a$, $R_b$, $R_c$, $R_d$, $R_e$, $R_f$, $R_g$ and $R_h$ are H (in other words, when $R_2$ and $R_3$ are taken together to form a $C_4$ alkyl, the $C_4$ alkyl is substituted with no more than six $C_1$–$C_{30}$ alkyl groups). Within the requirements of the above formulas, preferably $R_1$, $R_4$, $R_5$, $R_a$, $R_b$, $R_c$, $R_d$, $R_e$, $R_f$, $R_g$ and $R_h$, independently, is a $C_1$–$C_{10}$ alkyl group, more preferably a $C_1$–$C_3$ alkyl group, and most preferably $CH_3$. Preferred compounds include those wherein, in formulas [Ic] and [IIc]:

$R_1$ is $CH_3$, $R_4$ is H, $R_5$ is $CH_3$, $R_a$ is $CH_3$, $R_b$ is $CH_3$, $R_c$ is $CH_3$, $R_d$ is H, $R_e$ is $CH_3$, and $R_f$ is $CH_3$;

$R_1$ is $CH_3$, $R_4$ is H, $R_5$ is $CH_3$, $R_a$ is $CH_3$, $R_b$ is $CH_2CH_3$, $R_c$ is H, $R_d$ is H, $R_e$ is $CH_3$, and $R_f$ is $CH_3$; and $R_1$ is $CH_3$, $R_4$ is H, $R_5$ is $CH_3$, $R_a$ is $CH_3$, $R_b$ is $CH_3$, $R_c$ is H, $R_d$ is H, $R_e$ is $CH_3$, and $R_f$ is $CH_3$;

and those wherein, in formulas [Id] and [IId]:

$R_1$ is $CH_3$, $R_4$ is H, $R_a$ is $CH_3$, $R_5$ is $CH_3$, $R_b$ is $CH_3$, $R_c$ is H, $R_d$ is H, $R_e$ is $CH_3$, $R_f$ is H, $R_g$ is $CH_3$ and $R_h$ is $CH_3$; and $R_1$ is $CH_3$, $R_4$ is H, $R_5$ is $CH_3$, $R_a$ is $CH_3$, $R_b$ is $CH_3$, $R_c$ is H, $R_d$ is H, $R_e$ is H, $R_f$ is H, $R_g$ is $CH_3$ and $R_h$ is $CH_3$.

In a further preferred class of Formula [I] and [II] compounds, $R_3$ and $R_4$, taken together, are a $C_3$–$C_4$ alkyl which may be, if desired, substituted with one or more $C_1$–$C_{30}$ alkyl groups, such as the Formula [I] compounds

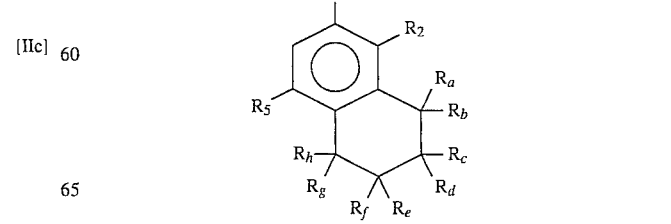

and the corresponding Formula [II] compounds

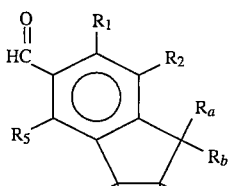 [IIe]

and

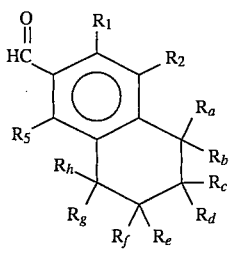 [IIf]

wherein: $R_1$, $R_2$ and $R_5$, are as previously defined, and wherein:

$R_a$, $R_b$, $R_c$, $R_d$, $R_e$, $R_f$, $R_g$ and $R_h$ are, independently, H or a $C_1$–$C_{30}$ alkyl group, provided that in Formulas [If] and [IIf], at least two of $R_a$, $R_b$, $R_c$, $R_d$, $R_e$, $R_f$, $R_g$ and $R_h$ are H (in other words, when $R_3$ and $R_4$ are taken together to form a $C_4$ alkyl, the $C_4$ alkyl is substituted with no more than six $C_1$–$C_{30}$ alkyl groups). Within the requirements of the above formulas, preferably $R_1$, $R_2$, $R_5$, $R_a$, $R_b$, $R_c$, $R_d$, $R_e$, $R_f$, $R_g$ and $R_h$, independently, is a $C_1$–$C_{10}$ alkyl group, more preferably a $C_1$–$C_3$ alkyl group, and most preferably $CH_3$.

In still another preferred class of Formula [I] and [II] compounds, $R_4$ and $R_5$, taken together, are a $C_3$–$C_4$ alkyl which may, if desired, be substituted with one or more $C_1$–$C_{30}$ alkyl groups, such as the Formula [I] compounds

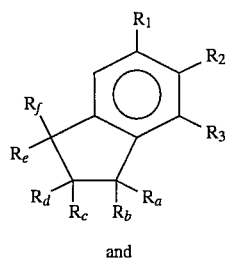 [Ig]

and

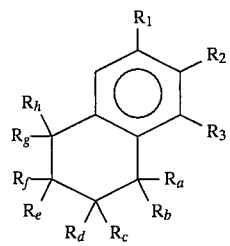 [Ih]

and the corresponding Formula [II] compounds

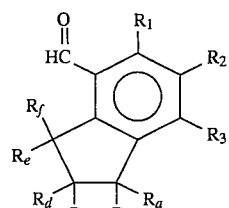 [IIg]

and

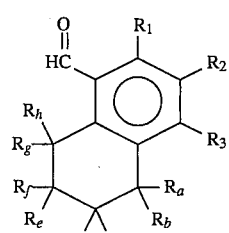 [IIh]

wherein $R_1$, $R_2$ and $R_3$, are as previously defined, and wherein:

$R_a$, $R_b$, $R_c$, $R_d$, $R_e$, $R_f$, $R_g$ and $R_h$ are, independently, H or a $C_1$–$C_{30}$ alkyl group, provided that in Formulas [If] and [IIf], at least two of $R_a$, $R_b$, $R_c$, $R_d$, $R_e$, $R_f$, $R_g$ and $R_h$ are H (in other words, when $R_4$ and $R_5$ are taken together to form a $C_4$ alkyl, the $C_4$ alkyl is substituted with no more than six $C_1$–$C_{30}$ alkyl groups). Within the requirements of the above formulas, preferably $R_1$, $R_2$, $R_3$, $R_a$, $R_b$, $R_c$, $R_d$, $R_e$, $R_f$, $R_g$ and $R_h$, independently, is a $C_1$–$C_{10}$ alkyl group, more preferably a $C_1$–$C_3$ alkyl group, and most preferably $CH_3$.

The foregoing preferred formylated indanes of Formulas [IIa], [IIc], [IIe] and [IIg], and the foregoing preferred formylated tetralins of Formulas [IIb], [IId], [IIf] and [IIh], above, may be employed in a highly useful manner, for example, as agents or additives for the perfumery and fragrance industries. The compound 1,1,2,3,3,4,6- heptamethylindan-5-carboxaldehyde is an especially important musk aroma compound for the perfumery and fragrance industries.

As another preferred class of Formula [I] and Formula [II] compounds, preferably $R_1$ is a $C_1$–$C_{10}$ alkyl, more preferably a $C_1$–$C_3$ alkyl, most preferably $CH_3$. As another preferable class, preferably $R_2$ is H or a $C_1$–$C_{10}$ alkyl, more preferably H or a $C_1$–$C_3$ alkyl, most preferably H or $CH_3$. In a further preferable class, preferably $R_3$ is H or a $C_1$–$C_{10}$ alkyl, more preferably H or a $C_1$–$C_3$ alkyl, most preferably H or $CH_3$. In another preferable class, preferably $R_4$ is H or a $C_1$–$C_{10}$ alkyl, more preferably H or a $C_1$–$C_3$ alkyl, most preferably H or $CH_3$. As a still further preferable class, preferably $R_5$ is a $C_1$–$C_{10}$ alkyl, more preferably a $C_1$–$C_3$ alkyl, most preferably $CH_3$. Also preferred are any and all combinations of the foregoing preferred classes.

A further preferable class of compounds of Formulas [I] and [II] are those wherein $R_3$ is a $C_1$–$C_{30}$ alkyl or a $C_1$–$C_{30}$ alkoxy (that is, wherein $R_3$ is other than H), especially a $C_1$–$C_{30}$ alkyl. This results in at least a 1,3,5 substitution pattern on the aromatic ring, which is one of the highly preferred substitution patterns for the compounds of Formulas [I] and [II] of the present invention.

A still further preferable class of the compounds of Formulas [I] and [II] includes those wherein:

$R_1$ is a $C_1$–$C_{10}$ alkyl;

$R_2$ is H or a $C_1$–$C_{10}$ alkyl;

or $R_1$ and $R_2$, taken together, are a $C_3$–$C_4$ alkyl which may, if desired, be substituted with one or more $C_1$–$C_{10}$ alkyl groups;

$R_3$ is H or a $C_1$–$C_{10}$ alkyl;

or $R_2$ and $R_3$, taken together, are a $C_3$–$C_4$ alkyl which may, if desired, be substituted with one or more $C_1$–$C_{10}$ alkyl groups;

$R_4$ is H or a $C_1$–$C_{10}$ alkyl;

or $R_3$ and $R_4$, taken together, are a $C_3$–$C_4$ alkyl which may, if desired, be substituted with one or more $C_1$–$C_{10}$ alkyl groups; and $R_5$ is a $C_1$–$C_{10}$ alkyl;

or $R_4$ and $R_5$, taken together, are a $C_3$–$C_4$ alkyl which may, if desired, be substituted with one or more $C_1$–$C_{10}$ alkyl groups.

Still another preferable class includes the Formula [I] and [II] compounds wherein:

$R_1$ is a $C_1$–$C_3$ alkyl;

$R_2$ is H or a $C_1$–$C_3$ alkyl;

or $R_1$ and $R_2$, taken together, are a $C_3$–$C_4$ alkyl which may, if desired, be substituted with one or more $C_1$–$C_3$ alkyl groups;

$R_3$ is H or a $C_1$–$C_3$ alkyl;

or $R_2$ and $R_3$, taken together, are a $C_3$–$C_4$ alkyl which may, if desired, be substituted with one or more $C_1$–$C_3$ alkyl groups;

$R_4$ is H or a $C_1$–$C_3$ alkyl;

or $R_3$ and $R_4$, taken together, are a $C_3$–$C_4$ alkyl which may, if desired, be substituted with one or more $C_1$–$C_3$ alkyl groups; and $R_5$ is a $C_1$–$C_3$ alkyl;

or $R_4$ and $R_5$, taken together, are a $C_3$–$C_4$ alkyl which may, if desired, be substituted with one or more $C_1$–$C_3$ alkyl groups.

Another preferable class includes the Formula [I] and [II] compounds wherein:

$R_1$ is a $C_1$–$C_3$ alkyl;

$R_2$ is H or a $C_1$–$C_3$ alkyl;

$R_3$ is H or a $C_1$–$C_3$ alkyl;

$R_4$ is H or a $C_1$–$C_3$ alkyl; and $R_5$ is a $C_1$–$C_3$ alkyl.

Such preferred compounds include those wherein, in formulas [I] and [II]:

$R_1$ is $CH_3$, $R_2$ is H, $R_3$ is $CH_3$, $R_4$ is H, and $R_5$ is $CH_3$;

$R_1$ is $CH(CH_3)_2$, $R_2$ is H, $R_3$ is $CH(CH_3)_2$, $R_4$ is H, and $R_5$ is $CH(CH_3)_2$;

$R_1$ is $CH_3$, $R_2$ is H, $R_3$ is $CH_3$, $R_4$ is $CH_3$ and $R_5$ is $CH_3$;

$R_1$ is $CH_3$, $R_2$ is $CH_3$, $R_3$ is H, $R_4$ is $CH_3$ and $R_5$ is $CH_3$; and $R_1$ is $CH_3$, $R_2$ is $CH_3$, $R_3$ is $CH_3$, $R_4$ is $CH_3$ and $R_5$ is $CH_3$.

A still further preferable class of Formulas [I] and [II] compounds are those wherein:

$R_1$ is $CH_3$;

$R_2$ is H or $CH_3$;

or $R_1$ and $R_2$, taken together, are a $C_3$–$C_4$ alkyl which may, if desired, be substituted with one or more $C_1$–$C_3$ alkyl groups;

$R_3$ is H or $CH_3$;

or $R_2$ and $R_3$, taken together, are a $C_3$–$C_4$ alkyl which may, if desired, be substituted with one or more $C_1$–$C_3$ alkyl groups;

$R_4$ is H or an $CH_3$;

or $R_3$ and $R_4$, taken together, are a $C_3$–$C_4$ alkyl which may, if desired, be substituted with one or more $C_1$–$C_3$ alkyl groups; and $R_5$ is $CH_3$;

or $R_4$ and $R_5$, taken together, are a $C_3$–$C_4$ alkyl which may, if desired, be substituted with one or more $C_1$–$C_3$ alkyl groups.

In accordance with the processes of the present invention, the aromatic compounds of Formula [I], are contacted with a halogenated compound selected from the group consisting of

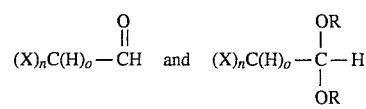

wherein:

X is Cl, F or Br;

each R is, independently, H, or a $C_1$–$C_{30}$ alkyl which may, if desired, be substituted with no more than one of the following groups: hydroxy, methoxy, ether, nitrile or nitro;

n is 2 or 3 (that is, the integer 2 or 3); and o is 3–n (that is, is the integer 3 minus the integer n).

By "no more than one" of the groups, it is meant that the alkyl R substitutent may be substituted with only one of the specified hydroxy, methoxy, nitrile or nitro groups, and there may be only one substitution of the alkyl with that group.

Preferably, X is Cl, F or Br, more preferably Cl or F, most preferably Cl. Also preferably n is 3 and o is 0. Moreover, preferably one of R is H and one of R is a $C_1$–$C_{30}$ alkyl which may, if desired, be substituted with no more than one of the following groups: hydroxy, methoxy, ether, nitrile or nitro More preferably, the halogenated compound is

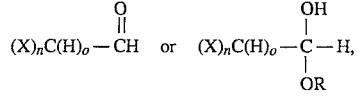

more preferably,

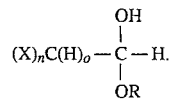

Further preferably, R is a $C_4$–$C_{12}$ alkyl, more preferably a $C_4$–$C_9$ alkyl, even more preferably a $C_5$–$C_8$ alkyl, wherein the alkyl may, if desired, be substituted with no more than one of the specified hydroxy, methoxy, nitrile or nitro groups. Preferably, the alkyl is not substituted with a hydroxy, methoxy, nitrile or nitro group (that is, is unsubstituted).

Most preferably, the halogenated compound is a chlorinated compound, that is, a compound wherein X is Cl especially a chlorinated compound which is chloral per se, wherein X is Cl, n is 3 and o is 0, specifically the compound which is

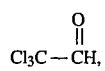

or a chlorinated compound which is a chloral hydrate or hemiacetal wherein X is Cl, n is 3 and o is 0, specifically the compounds which are

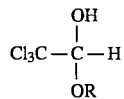

such as wherein R is H (such as the compound which is chloral hydrate), or methyl (such as the compound which is chloral methyl hemiacetal), or ethyl (such as the compound which is chloral ethyl hemiacetal), or propyl (such as the compound which is chloral propyl hemiacetal), or n-butyl (such as the compound which is chloral n-butyl hemiacetal), or iso-butyl (such as the compound which is chloral iso-butyl hemiacetal), or pentyl (such as the compound which is chloral pentyl hemiacetal), or n-pentyl (such as the compound which is chloral n-pentyl hemiacetal), or hexyl (such as the compound which is chloral hexyl hemiacetal), or iso-heptyl (such as the compound chloral iso-heptyl hemiacetal), or 1-octyl (such as the compound which is chloral 1-octyl hemiacetal), or 2-octyl (such as the compound which is chloral 2-octyl hemiacetal), or iso-octyl (such as the compound chloral iso-octyl hemiacetal), or iso-nonyl (such as the compound chloral iso-nonyl hemiacetal), or iso-decyl (such as the compound chloral iso-decyl hemiacetal), or dodecyl (such as the compound chloral dodecyl hemiacetal), or tridecyl (such as the compound chloral tridecyl hemiacetal), or iso-tridecyl (such as the compound chloral iso-tridecyl hemiacetal), or iso-hexadecyl (such as the compound chloral iso-hexadecyl hemiacetal), or iso-octadecyl (such as the compound chloral iso-octadecyl hemiacetal), or 2-ethyl-1-hexyl (such as the compound which is chloral 2-ethyl-1-hexyl hemiacetal), or 3-methyl- 2-butyl (such as the compound which is chloral 3-methyl- 2-butyl hemiacetal), or 2-methyl-butyl (such as the compound which is chloral 2-methyl-butyl hemiacetal), or 2-methyl- 1-butyl (such as the compound which is chloral 2-methyl- 1-butyl hemiacetal), or 3-methyl-butyl (such as the compound which is chloral 3-methyl-butyl hemiacetal), or 3-methyl-1-butyl (such as the compound which is chloral 3-methyl-1-butyl hemiacetal), or 2-methyl-1-propyl (such as the compound which is chloral 2-methyl-1-propyl hemiacetal), or 3,7-dimethyloctyl (such as the compound which is chloral 3,7-dimethyloctyl hemiacetal), or 2-methyl-pentyl (such as the compound which is chloral 2-methyl-pentyl hemiacetal), or 2-ethyl-butyl (such as the compound which is chloral 2-ethylbutyl hemiacetal), or 2,3-dimethyl-butyl (such as the compound which is chloral 2,3-dimethyl-butyl hemiacetal), or 2-ethyl-hexyl (such as the compound chloral 2-ethylhexyl hemiacetal), or 2,4,4-trimethyl-1-pentyl (such as the compound which is chloral 2,4,4-trimethyl-1-pentyl hemiacetal), or 3,5,5-trimethylhexyl (such as the compound which is chloral 3,5,5-trimethyl-hexyl hemiacetal), or 3,5,5-trimethyl- 1-hexyl (such as the compound which is chloral 3,5,5-trimethyl-1-hexyl hemiacetal), or methoxyethyl (such as the compound which is chloral methoxyethyl hemiacetal), or ethylene glycol (such as the compound which is chloral ethylene glycol hemiacetal), or mixtures thereof. Of all of the foregoing compounds, the most preferable is chloral 2-ethyl- 1-hexyl hemiacetal, chloral 3-methyl-1-butyl hemiacetal, chloral 2-methyl-1-butyl hemiacetal, chloral 2-methyl- 1-propyl hemiacetal, or mixtures of chloral 3-methyl1-butyl hemiacetal and chloral 2-methyl-1-butyl hemiacetal.

Another preferable halogenated compound is trifluoroacetaldehyde alkyl hemiacetal wherein X is F, n is 3 and o is 0, specifically the compounds which are

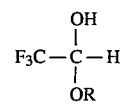

such as wherein R is ethyl (the compound which is trifluoroacetaldehyde alkyl hemiacetal).

The aromatic compound of Formula [I] is contacted with the subject halogenated compound in the presence of a Lewis acid. Any Lewis acid, that is, any non-protonic compound capable of accepting an electron pair in the present process of the invention, is suitable for use in the subject process. Preferable Lewis acids include metal halides such as titanium halides (including titanium chloride), aluminum halides (including aluminum chloride, aluminum bromide, aluminum iodide, monofluorodichloroaluminum, monobromodichloroaluminum and monoiododichloroaluminum), zinc halides (including zinc chloride), iron halides (including iron chloride), boron halides (including boron fluoride), and tin halides (including tin chloride). When employing an oxygenated aromatic compound starting material, that is, an aromatic compound of Formula [I] wherein $R_1$, $R_2$, $R_3$, $R_4$ or $R_5$ is $C_1$–$C_{30}$ alkoxy, preferable Lewis acids include metal alkoxides, such as titanium isopropylate. Particularly preferred are the metal halides. One preferred group of metal halides are titanium chloride, aluminum chloride, aluminum bromide, iron chloride, boron fluoride and tin chloride. Another preferred group of metal halides are titanium halides and aluminum halides, particularly titanium chloride and aluminum chloride.

A wide variety of bases, that is, compounds capable of neutralizing acids, such as the protonic acids (HCl, HF, HBr) which may be generated in the course of the present process, may also be employed in the subject process, as one skilled in the art would recognize, once armed with the present disclosure. Suitable bases include inorganic bases and organic bases. Exemplary inorganic bases include alkali metal or alkaline earth metal hydroxides, bicarbonates, carbonates, oxides, amides and hydrides, such as sodium hydroxide, potassium hydroxide, calcium hydroxide, lithium hydroxide, sodium bicarbonate, potassium bicarbonate, calcium bicarbonate, lithium bicarbonate, sodium carbonate, potassium carbonate, calcium carbonate, lithium carbonate, calcium oxide, sodium amide (sodamide), sodium hydride, potassium hydride, lithium hydride and calcium hydride. Exemplary organic bases include sodium alkoxides, potassium alkoxides, calcium alkoxides, lithium alkoxides, substituted pyridines, sodium diisopropyl amide and lithium diisopropyl amide. Although not intending to be bound by any theory of operation, not only does the base serve to move the reaction to completion, it is also believed that the use of a base in the present process minimizes side reactions, thereby allowing increased yield and recovery of the desired end products. In particular, it is theorized that the use of the base serves to neutralize the protonic acid in the reaction medium, which in turn increases reaction rate and reduces the number of possible protonic acid side reactions, allowing for higher product yield and recovery.

In a preferable embodiment, the subject process is carried out under conditions which, in addition to the use of the base, may serve to reduce the amount or concentration of protonic acid in solution in the reaction medium, thereby further adding to product yield and recovery by, it is theorized, increasing reaction rate and minimizing protonic acid dependent side reactions. This may be achieved by such means as using a low polarity solvent (to decrease the amount of the polar protonic acid in solution), a refluxing solvent (again, to force protonic acid gas or other gas out of solution), vigorous stirring (again, to force protonic acid gas or other gas out of solution), a gas sweep (that is, applying positive pressure to the headspace of the reaction using, preferably, an inert gas; to help drive off protonic acid gas or other gas), a vacuum (that is, applying negative pressure to the headspace of the reaction; again, to help drive off protonic acid gas or other gas), as well as combinations thereof. The foregoing are representative of conditions which minimize the amount or concentration of protonic acid in solution, and other such means of achieving this end will be readily apparent to those skilled in the art, once placed in possession of the present disclosure. These and any other such means are intended to be within the scope of the present invention. Use of a vacuum, especially at pressures between about 20 mbar and about 60 mbar, particularly a pressure of about 40 mbar, is preferred. Especially preferred combinations of the foregoing conditions include the use of a vacuum in combination with at least one additional condition, such as a vacuum assisted sweep, a refluxing solvent with a vacuum assist, etc. Such conditions may be employed throughout the entire process, or at any stage of the process. It is most preferable to employ the conditions which reduce the amount or concentration of protonic acid in solution during the entire process, or at least during the process steps where the aromatic starting material, halogenated compound and Lewis acid are combined and reacted (that is, at least up until base addition).

In general, the reaction is carried out in the presence of a solvent. The solvent may be an additional solvent, or, alternatively, if desired, the aromatic compound starting material may be employed in large excess, in lieu of an additional solvent. Preferably the solvent is an additional solvent. Suitable additional solvents will be readily apparent to those skilled in the art, once armed with the present disclosure, and include halogenated and unhalogenated aliphatic, alicyclic and aromatic hydrocarbon solvents. Exemplary unhalogenated solvents are the unhalogenated aliphatic solvents n-hexane, n-heptane, n-octane, and 2,2,4-trimethylpentane (iso-octane), the unhalogenated alicyclic solvent cyclohexane, and the unhalogenated aromatic solvents benzene, nitrobenzene, toluene, ethylbenzene and xylene. Representative of the halogenated solvents are the halogenated aliphatic solvents methylene chloride (dichloromethane), chloroform, carbon tetrachloride, ethylene chloride, 1,1,1-trichloroethane, 1,1,2-trichloroethane, 1,1,2,2-tetrachloroethane, 1,2-dichloroethylene, trichloroethylene, tetrachloroethylene, 1,2,3-trichloropropane, amyl chloride, and ethylene bromide, and the halogenated aromatic solvents monochlorobenzene, dichlorobenzene (including ortho-dichlorobenzene), bromobenzene, and fluorobenzene. Particularly preferred for reasons of safety are the unhalogenated aliphatic, unhalogenated alicyclic and unhalogenated aromatic compounds, particularly the unhalogenated aliphatic, unhalogenated alicyclic compounds. Especially preferred solvents are n-hexane, cyclohexane, and 2,2,4-trimethylpentane (iso-octane). Other suitable polar and nonpolar nonreactive solvents will be readily apparent to those skilled in the art.

With regard to choosing a particular solvent and halogenated compound combination, it is noted that the halogenated hemiacetal compounds are generally more soluble in halogenated hydrocarbon solvents, such as, for example, in methylene chloride, with solubility leading to better process results. A number of halogenated compounds, may, however, be used in combination with unhalogenated hydrocarbon solvents with good solubility and outstanding results. For example, the halogenated compounds chloral 2-ethylhexyl hemiacetal, chloral 3-methyl-1-butyl hemiacetal or chloral 2-methyl-1-butyl hemiacetal may be employed with excellent results in combination with such unhalogenated hydrocarbon solvents as iso-octane and cyclohexane. These and other suitable combinations of solvents and halogenated compounds will be readily apparent to those skilled in the art, once armed with the present disclosure.

The process may be carried out over a wide temperature range. Typically, however, the process is carried out at temperatures ranging between about −40° C. to about 50° C., preferably between about −35° C. and about 25° C., more preferably between about −20° C. and about 5° C., and most preferably between about −15° C. and about 0° C.

The pressure at which the reaction is carried out is not critical. If the reaction is carried out in a sealed vessel, autogenous pressure is acceptable, although higher or lower pressures, if desired, may be employed. The reaction may also be carried out at atmospheric pressure in an open reaction vessel, in which case the vessel is preferably equipped with a moisture trap to prevent significant exposure of the Lewis acid to moisture. The reaction may take place in an oxygen atmosphere or an inert atmosphere as in the presence of a gas such as nitrogen, argon and the like, the type of atmosphere also not being critical. Preferably, however, the atmosphere employed is an inert atmosphere, to minimize possible autoxidation of the resultant formylated aromatic compound. Also preferably, the reaction is carried out in a vacuum, preferably at pressures between about 20 mbar and about 60 mbar, especially at about 40 mbar.

Reaction time is generally short, and is often dictated by the kind of equipment employed. Sufficient time must be provided, however, for thorough contacting of the aromatic compound starting material, the halogenated compound, the Lewis acid and the base. Generally, the reaction proceeds to completion in about 4 to about 8 hours, although shorter or longer reaction times may be experienced.

The molar proportions of the reagents employed in the subject process may be varied over a relatively wide range, the precise amounts of the reagents being dependent upon such factors as the solvent employed, and the particular aromatic starting material, halogenated compound, Lewis acid and base used, as well as other reaction conditions such as time, temperature, pressure, atmosphere, etc. Suitable reagent amounts will be well within the ambit of those skilled in the art, once armed with the present disclosures. By way of general guidance, however, typically a slight molar deficit to a slight molar excess of the halogenated compound relative to the aromatic compound starting material is employed. For example, a suitable molar ratio of halogenated compound to aromatic compound starting material may be about 0.5:1 to about 1:2, more preferably about 0.75:1 to about 1:1.6. Also, typically an equimolar amount to a slight molar excess of Lewis acid relative to the halogenated compound is employed. A suitable molar ratio of Lewis acid to halogenated compound may be about 1:1 to about 1:2, more preferably about 1:1 to about 1:1.6. Also by way of general guidance, base is preferably added in an amount sufficient to make and keep the reaction medium alkaline. To achieve this effect, typically a greater than equimolar amount of base to halogenated compound is employed. For example, a ratio of about 1.5:1 to about 4:1, more preferably about 2:1 to about 3:1, base to halogenated compound, may be used.

The subject process may be carried out in any suitable vessel which provides sufficient contacting between the Lewis acid and the other reagents. For simplicity, a stirred batch reactor can be employed. The reaction vessel used should be resistant to the possible corrosive nature of the Lewis acid, such as a glass-lined vessel.

In carrying out the subject process, the base should be added to the reaction medium after the aromatic compound starting material, halogenated compound and Lewis acid are added. The aromatic compound starting material, halogenated compound and Lewis acid (and any solvent) may be added to the vessel in any order. In accordance with the preferable protocol, however, the Lewis acid and any solvent are added first, and sufficient time is allowed for the Lewis acid to become substantially dissolved in the solvent, followed by addition of the remaining reagents, with the base added last. Typically, about 1 to about 30 minutes are needed for the Lewis acid to dissolve substantially in the solvent. Base is added last, typically about 3 to about 6 hours after the aromatic compound starting material, halogenated compound and Lewis acid have been added. The terminology "followed by", in the context of the process of contacting an aromatic compound with a halogenated compound in the presence of a Lewis acid, "followed by" a base, denotes that the base is added last, that is, after the aromatic compound, halogenated compound and Lewis acid.

In a preferable embodiment, the reaction mixture is subjected to an aqueous quench, preferably using cold water or crushed ice, prior to base addition. After the resultant phase separation, the aqueous layer is separated and the base added to the remaining organic layer. Alternatively, although not preferred, the reaction mixture may be subjected to an aqueous quench concurrently with base addition, or, if desired, although again not preferred, there may be no aqueous quench.

Following completion of the subject process, end product may be recovered from the reaction mixture by aqueous quenching, preferably using cold water or crushed ice, followed by processing in the usual manner for Friedel-Crafts reactions, to extract the formylated aromatic compounds. Suitable extraction protocol is described, for example, in George A. Olah, *Friedel-Crafts And Related Reactions*, Vols. 1 and 2 (Interscience Publishers, John Wiley and Sons, New York, N.Y. 1964) and Rieche et al., Aromatic Aldehydes. Mesitaldehyde, *Organic Syntheses*, Collective Vol. 5, pp. 49–50 (1973), the disclosures of each of which are hereby incorporated by reference in their entirety. Typically, following quenching and the resultant phase separation, the organic layer is washed an additional time with water to aid in removal of the Lewis acid. One or more additional washings may be carried out with dilute alkali solution, if desired, to further aid Lewis acid removal. The resultant product may be further purified, if desired, by subjecting it to reduced pressure fractional distillation, commercial chromatographic separation, or other separation means known to those skilled in the art.

The starting materials for the processes of the present invention may be obtained commercially, or prepared using numerous well known procedures. The preparation of indane or tetralin aromatic compound starting materials are disclosed, for example, in Frank, U.S. Pat. Nos. 4,877,911, 4,877,914, 4,877,910, 4,877,916, 4,877,915, 4,877,913, 4,877,912 and 5,087,785, Carpenter, U.S. Pat. Nos. 2,897, 237 and 2,800,511, Cobb et al., U.S. Pat. No. 4,551,573, Japanese Patent No. SHO 57-40420, Wood, U.S. Pat. No. 3,246,044, Wood et al., U.S. Pat. No. 3,856,875, Sato et al., U.S. Pat. No. 4,284,818, Kahn, U.S. Pat. No. 3,379,785, Suzukamo et al., U.S. Pat. No. 4,767,882, Fehr et al., U.S. Pat. No. 5,162,588, Willis et al., U.S. Pat. No. 4,605,778, Traas et al., U.S. Pat. No. 4,352,748, Gonzenbach, U.S. Pat. No. 4,908,349, European Patent Application Publication No. 0 393 742, European Patent Application Publication No. 0 301 375, Japanese Patent No. SHO 57-40420, Fehr et al., Helv. Chim. Acta, Vol. 72, pp. 1537–1553 (1989), and Bedoukian, Paul Z., *Perfumery and Flavoring Synthetics*, 3rd ed., pp. 334–336, Allured Publishing Corporation, Wheaton, Ill. (1986), the disclosures of each of which are hereby incorporated herein by reference, in their entirety. Other aromatic compound starting materials, as well as suitable halogenated compounds, Lewis acids, bases and solvents, may be obtained from, for example, Aldrich Chemical Company, Inc., 940 West Saint Paul Avenue, Milwaukee, Wis. 53233, Wacker Chemicals USA, Inc., 50 Locust Avenue, New Canaan, Conn. 06840, R. W. Greeff & Company, Inc., 777 West Putnam Avenue, Greenwich, Conn. 06830, or other commercial sources. The hemiacetal halogenated compounds may also be prepared by reacting the halogenated compound (i.e., choral, floral or bromal) with water or with the desired alcohol, to yield the corresponding hydrate (reaction with water) or hemiacetal (reaction with an alcohol) compound. For example, chloral may be reacted with iso-amyl alcohol (which is a mixture of 3-methyl-1-butanol and 2-methyl-1-butanol) to produce choral 3-methyl-1-butyl hemiacetal and chloral 2-methyl-1-butyl hemiacetal. Alcohols suitable for reaction halogenated compounds may be obtained from, for example, Exxon Chemical Co., P.O. Box 3272, Houston, Tex. 77253, Hoechst Celanese Corporation, Specialty Chemicals Group, 77 Center Drive, Charlotte, N.C. 28201, or other commercial sources.

The subject process provides an efficient and effective means of preparing formylated aromatic compounds which may have utility in a wide variety of applications, for example, as fragrance compounds, and as intermediates in organic synthesis, etc. For example, the indane or tetralin formylated aromatic compounds may be used as perfumery agents or additives to fragrance compositions, or they may be further oxidized to yield a formate ester and then employed in such uses. Various formylated aromatics may also be used, for example, as intermediates in the preparation of acids, dyestuffs, flavor compounds, pharmaceuticals and agrichemicals. These and other uses of the formylated aromatic compounds of the present invention will be apparent to those skilled in the art, once placed in possession of the present invention.

Many of the prior art processes for the formylation of aromatics employ difficult reaction schemes, require expensive or complex equipment, necessitate the use of costly, difficult to obtain or hazardous reagents, provide unsatisfactory yields, and/or are applicable to only a select number of aromatic compounds. The present invention addresses many of these drawbacks of the prior art and provides a process for the formylation of a wide variety of aromatic compounds in a relatively, simple, efficient, safe and economically feasible fashion.

The invention is further described in the following actual examples, which illustrate the process of the present invention. These examples are intended to be illustrative only, and are not to be construed as limiting the scope of the appended claims.

EXAMPLES

Example 1

This example demonstrates chloral adduction to mesitylene in the presence of titanium chloride in hexane to from the carbinol, and decomposition of the carbinol to the aldehyde in sodium hydroxide.

To a clean, dry 3-necked round-bottom reaction flask under dry nitrogen, 0.5 g (0.0042 mole) of mesitylene and 12 ml of dry n-hexane was added by syringe. Stirring was initiated. The solution was cooled using a dry-ice isopropanol bath to −15° C. and 0.87 g (0.0046 mole) of $TiCl_4$ was added to the solution by syringe. The solution was stirred an additional 10 minutes, and 0.67 g (0.00455 moles) of chloral was added dropwise at a rate which allowed the temperature to be maintained at −15° C.+/−3° C. The reaction solution was stirred for an additional 6 hours, with progress being monitored by G.C. analysis.

A sample (0.25 ml) was taken after the 6 hours, quenched in water (0.3 ml), and solid NaOH (0.3 g) and isopropanol (3 ml) added. The sample was mixed with a pipet and placed in a 70° C. hot water bath for 10 minutes. The sample was then poured into 20 ml of water and extracted with 3 ml of dichloromethane. The resultant dichloromethane solution was filtered through anhydrous granulated $K_2CO_3$ into a vial and analyzed on a 5890A Hewlett-Packard FID Gas-Chromatograph. The column was a 30 meter DB-1 glass column 0.59 mm id coated with 1.5 micrometers of DB-1. The column temperature program was as follows: 70° C. for 8 minutes, 5° C./minute to 100° C. hold 100° C. for 1 minute, 10° C./minute to 235° C., and hold 235° C. for 10 minutes. The injection port temperature was 235° C. and the detector was 235° C. The carrier gas was dry nitrogen flowing at 15 ml/minute through the column. Under these conditions mesitylene showed a retention time of 6.5 minutes, and mesitylaldehyde a retention time of 16.8 minutes.

The sample taken at 6 hours and worked up as described above was determined by GC analysis to contain about 4% mesitylene and about 89% mesitylaldehyde.

Example 2

This example demonstrates adduction of chloral methyl hemiacetal to mesitylene in the presence of titanium chloride in methylene chloride to form the carbinol, and decomposition of the carbinol to the aldehyde in sodium hydroxide.

Chloral methyl hemiacetal was prepared by slowly adding 0.67 g (0.00455 mole) chloral to 0.5 g (0.00469 mole) methanol at room temperature. The exotherm was moderated by slow addition of the chloral.

The procedures of Example 1 were then substantially followed, except that the chloral methyl hemiacetal was used in place of chloral, and $CH_2Cl_2$ replaced the hexane solvent on an equal volume basis. Specifically, the hemiacetal 0.87 g (0.00459 mole) was added to a −15° C. reaction solution containing $TiCl_4$, 0.5 g (0.00416 mole) mesitylene, and 3 ml $CH_2Cl_2$, over a period of about 5 minutes. After the addition, the reaction solution was maintained at −15° C. for 6 hours, and samples were withdrawn at 15 minutes, 2 hours and 6 hours, subjected to an aqueous quench, treated with NaOH, and worked up substantially as described in Example 1. The first sample taken at 15 minutes showed on GC analysis about 56% mesitylene and about 44% mesitylaldehyde. The 2 hour GC sample showed about 22% mesitylene and about 78% mesitylaldehyde. The 6 hour GC sample showed about 7% mesitylene and about 92% mesitylaldehyde.

Example 3

This example demonstrates the adduction of chloral 2-ethyl-1-hexyl hemiacetal to mesitylene in the presence of titanium chloride in iso-octane (2,2,4-trimethylpentane) to form the carbinol, and decomposition of the carbinol to the aldehyde in sodium hydroxide.

First, into a test tube was placed 1.2 g (0.00921 mole) of 2-ethyl-1-hexanol. To this alcohol was added dropwise 1.4 g (0.00950 mole) of chloral. The solution heated to about 75° C. as the chloral was added. The resulting chloral 2-ethyl-1-hexyl hemiacetal was allowed to cool to room temperature (25° C.).

Next, to a clean, dry three-necked 50-ml reaction flask, filled with dry nitrogen, was added 7 ml of iso-octane (2,2,4-trimethylpentane) and 1.3 ml, 1.8 g (0.00935 mole) of $TiCl_4$. The iso-octane/$TiCl_4$ solution was then cooled to −5° C., and the chloral 2-ethyl-1-hexyl hemiacetal solution was added. The solution was then stirred for 5 minutes, and 1.0 g (0.00833 mole) of mesitylene was added dropwise over one minute.

The reaction mixture was stirred at −5° C. for 2 hours and 22 minutes, while using a nitrogen gas sweep. Samples (0.25 ml) were removed at 4 minutes and 1 hour and 4 minutes, quenched in water, and extracted with 3 ml of $CH_2Cl_2$. No NaOH/isopropanol treatment was provided. Each $CH_2Cl_2$ extract was washed with water and filtered through $K_2CO_3$ prior to GC analysis. The 4 minute sample showed about 8% 2,2,2-trichloro-1-(2',4',6'-trimethylphenyl)ethanol and about 90% unconverted mesitylene. The 64 minute sample showed about 88% of 2,2,2-trichloro-1-(2', 4', 6'-trimethylphenyl)ethanol, about 7% of unconverted mesitylene, and about 2% of α,α-dichloroacetyl-(2,4,6-trimethylbenzene).

A sample (0.25 ml) of the final product mixture was set aside, and the remaining final product mixture was characterized by quenching the reaction mixture at 2 hours and 22 minutes with about 20 ml of water, adding about 20 ml of $CH_2Cl_2$, extracting the aqueous layer with $CH_2Cl_2$, washing the $CH_2Cl_2$ layer with about 20 ml of water and drying the organic layer by passing it through anhydrous $K_2CO_3$ prior to GC analysis. GC analysis showed a product mixture containing about 93% 2,2,2-trichloro-1-(2',4',6'-trimethylphenyl) ethanol, about 1 percent mesitylene, and about 2% α,α-dichloroacetyl-( 2,4,6-trimethylbenzene).

The 0.25 ml sample of final product mixture which had been set aside was treated with NaOH and worked up substantially as described in Example 1. GC analysis showed the presence of about 94% of the desired mesitylaldehyde and about 1% mesitylene.

Example 4

This example demonstrates the adduction of chloral to mesitylene in the presence of titanium chloride in hexane to form the carbinol, and decomposition of the carbinol to the aldehyde in sodium hydroxide.

To a 25 ml 3-necked round-bottom reaction-flask purged with dry nitrogen was placed 0.5 g (0.0042 mole) of mesitylene and 12 ml of hexane. The solution was stirred ad cooled to −15° C., and 0.87 g (0.00459 mole) of $TiCl_4$ was added. The solution was stirred for 5 minutes and 0.67 g (0.00455 mole) of chloral was added dropwise at a rate such that the temperature did not exceed −15 C.+/−2° C.

The reaction was stirred for 6 hours and small samples (0.25 ml) were taken at 40 minutes, 2 hours, and 6 hours for GC analysis. The GC samples were subjected to an aqueous quench, treated with NaOH, and worked-up substantially as described in Example 1. The 40 minute sample showed about 33% mesitylene and about 62% mesitaldehyde. The 2 hour sample showed about 20% mesitylene and about 78% mesitaldehyde. The 6 hour sample showed about 9% mesitylene and about 89% mesitylaldehyde.

Example 5

This example demonstrates the adduction of chloral to 1,3,5-tri-iso-propylbenzene in the presence of titanium chloride in hexane to form the carbinol, and decomposition of the carbinol to the aldehyde in sodium hydroxide.

The procedures in Example 4 were substantially followed, except that 0.25 g (0.00122 mole) of 1,3,5-tri-iso-propylbenzene was used in place of mesitylene, and about 0.2 g (0.00136 mole) of chloral, 0.25 g (0.00132 mole) $TiCl_4$, and 6 ml of hexane were used. GC samples were removed at 40 minutes and at 6 hours, subjected to an aqueous quench, treated with NaOH, and worked up substantially as described in Example 1. The 40 minute GC sample showed about 97% 1,3,5-tri-iso-propylbenzene and about 2% 2,4,6-tri-iso-propylbenzaldehyde. The 6 hour GC sample contained about 94% of the tri-iso-propylbenzene and about 6% of the 2,4,6-tri-iso-propylbenzaldehyde.

Example 6

This example demonstrates the adduction of chloral methyl hemiacetal to 1,2,3,5-tetramethylbenzene in the presence of titanium chloride in methylene chloride to form the carbinol.

Example 2 was substantially repeated except that 1.87 ml (2.81 g, 0.0190 mole) of chloral and 0.4 g (0.0124 mole) of methanol were used to prepare the chloral methyl hemiacetal, 1.55 g (0.0116 mole) of 1,2,3,5-tetramethylbenzene was employed instead of mesitylene, 1.78 ml (2.43 g, 0.0128 mole) of $TiCl_4$ and 7 ml of $CH_2Cl_2$ were used, and no decomposition of the carbinol to the aldehyde using base was carried out. A small sample (0.25 ml) was removed at 18 minutes after the addition of the hemiacetal to the aromatic and subjected to an aqueous quench. GC analysis showed the sample to contain about 24% 1,2,3,5-tetramethyl-benzene and about 75% 1,2,2,2-tetrachloro-1-(2',3',4', 6'-tetramethylphenyl)-ethanol.

Example 7

This example demonstrates the adduction of chloral to 1,1,2,3,3,4,6-heptamethylindane (HMI) in the presence of titanium chloride in methylene chloride to form the carbinol, and decomposition of the carbinol to the aldehyde in sodium hydroxide.

Example 1 was substantially followed except that 0.5 g (0.0023 mole) of 1,1,2,3,3,4,6-heptamethylindane (69.6% purity) was used instead of mesitylene, and 0.37 g (0.00251 mole) of chloral, 0.48 g (0.00253 mole) of $TiCl_4$, and 12 ml of $CH_2Cl_2$ were used. GC analysis of the reaction solution at two hours, after aqueous quench and treatment with NaOH, and work up as in Example 1, showed the presence of about 21% HMI and about 61% 1,1,2,3,3,4,6-heptamethylindane-5-carboxaldehyde (HMI 5-carboxaldehyde).

Example 8

This example demonstrates the adduction of chloral to 1,1,2,3,3,4,6-heptamethylindane (HMI) in the presence of titanium chloride in hexane to form the carbinol, and decomposition of the carbinol to the aldehyde in sodium hydroxide.

Example 2 was substantially repeated except that 0.5 g of HMI (0.00231 mole, 69.6% purity) was used in place of mesitylene, and 0.37 g (0.00251 mole) of chloral, 0.48 g (0.00253 mole) of $TiCl_4$, and 12 ml of hexane were used, and the reaction was carried out at a temperature of $-35°$ C. GC samples (0.25 ml) were removed at 40 minutes, 2 hours, 4 hours, and 6 hours, subjected to an aqueous quench, treated with NaOH, and worked up substantially as described in Example 1. The 40 minute GC sample showed about showed the presence of about 53% HMI and about 12% of 1,1,2,3, 3,4,6-heptamethylindane- 5-carboxaldehyde (HMI 5-carboxaldehyde). GC analysis of the 2 hour sample showed the presence of about 49% HMI and about 24% of the HMI 5-carboxaldehyde. The 4 hour GC sample showed the presence of about 36% HMI and about 32% of the HMI 5-carboxaldehyde. The 6 hour GC sample showed the presence of about 29% HMI and about 39% of the 5-carboxaldehyde.

Example 9

This example demonstrates the adduction of chloral 2-ethyl-1-hexyl hemiacetal to 1,1,2,3,3,4,6-heptamethylindane (HMI) in the presence of titanium chloride in iso-octane (2,4,4-trimethylpentane) to form the carbinol, and decomposition of the carbinol to the aldehyde in sodium hydroxide.

To a clean, dry three-necked round-bottom reaction flask was added, under a nitrogen atmosphere, 24 ml of iso-octane (2,4,4-trimethylpentane) and 7.2 g (0.00325 mole) of HMI. The mixture was stirred with a paddle-blade stirrer and cooled to 5° C. While maintaining the temperature at 5° C., 5.2 ml (7.128 g, 0.0376 mole) of $TiCl_4$ was added dropwise. The solution was stirred for about 15 minutes until it became homogeneous, and the solution was cooled to $-15°$ C. The 2-ethyl- 1-hexyl hemiacetal of chloral, prepared substantially as described in Example 3 using about 4.8 g (0.0369 mole) of 2-ethyl-1-hexanol and 5.6 g (0.0380 mole) of chloral, was then added dropwise to the $-15°$ C. HMI/$TiCl_4$/iso-octane solution over a period of about ten minutes. The temperature was maintained between $-17°$ C. to $-13°$ C. during the addition.

The reaction was stirred for 5 hours and small samples (0.25 ml) were taken at 1 hour, 2 hours, 3 hours and 5 hours for GC analysis. The GC samples were subjected to an aqueous quench, treated with NaOH, and worked-up substantially as described in Example 1. The 1 hour GC sample showed about 28% HMI and about 71% 1,1,2,3,3,4,6-heptamethylindane- 5-carboxaldehyde (HMI 5-carboxaldehyde). The 2 hour GC sample showed about 16% HMI and about 83% HMI 5-carboxaldehyde. At 3 hours, the GC sample showed about 10% HMI and about 90% HMI 5-carboxaldehyde. GC analysis of the 5 hour sample showed about 7% HMI and about 92% of the HMI 5-carboxaldehyde.

Example 10

This example demonstrates the adduction of chloral 2-ethylhexyl hemiacetal to 3,5-dimethylanisole in the presence of titanium chloride in iso-octane (2,4,4-trimethylpentane) to form the carbinol, and decomposition of the carbinol to the aldehyde in sodium hydroxide.

Into a 25 ml three-necked round-bottom flask purged with nitrogen was charged 1 g (0.00735 mole) of 3,5-dimethylanisole and 5 ml of iso-octane (2,4,4-trimethylpentane). The solution was cooled with stirring to −15° C. and 1.53 g (0.00807 mole) of $TiCl_4$ was slowly added using a syringe. The solution was then stirred for an additional 15 minutes at −15° C.

In a separate reaction vessel, the chloral 2-ethylhexyl hemiacetal was prepared from 1.05 g 2-ethyl-1-hexanol and 1.19 g (0.00807 mole) chloral substantially as described in Example 3. This material was dispersed in 1 ml of iso-octane and was added dropwise over twenty minutes to the 3,5-dimethylanisole/iso-octane/$TiCl_4$ mixture. A sticky material precipitated, but the reaction solution was stirred at −15° C. for 4.5 hours before being with quenched with water, treated with NaOH, and worked-up substantially as described in Example 1.

GC analysis of the product mixture showed that it contained about 40% 3,5-dimethylanisole and about 53% of a combined yield of two aldehydes, 2-methoxy-4,6-dimethylbenzaldehyde and 4-methoxy-2,6-dimethylbenzaldehyde.

Example 11

This example demonstrates the adduction of chloral to mesitylene in the presence of aluminum chloride in $CH_2Cl_2$ to form the carbinol.

Into a clean, dry 25 ml three-necked, round-bottom reaction flask was added 6 ml of $CH_2Cl_2$, 1 g (0.0083 mole) of mesitylene and 0.22 g (0.00165 mole) of $AlCl_3$. The mixture was stirred under nitrogen and cooled to −15° C. After 5 minutes, the pressure within the reaction flask was reduced to 140 mbar, and 1.35 g (0.00916 mole) of chloral was added dropwise at such a rate that the temperature remained between −13° C. and −17° C.

A small sample (0.25 ml) was removed after 6 hours, quenched in water, and extracted with 3 ml of $CH_2Cl_2$. No NaOH/isopropanol treatment was provided. Each $CH_2Cl_2$ extract was washed with water and filtered through $K_2CO_3$ prior to GC analysis, substantially as provided in Example 3. GC analysis of the resultant mixture showed the presence of about 29% mesitylene, about 8% 1,2,2,2-tetrachloro-1-[2',4',6'-trimethylphenyl]ethane, and 59% 2,2,2-trichloro-1-(2',4',6'-trimethylphenyl) ethanol.

The disclosures of each patent and publication cited or described herein are hereby incorporated herein by reference, in their entirety.

Various modifications of the invention, in addition to those shown and described herein, will be readily apparent to those skilled in the art from the foregoing description. Such modifications are also intended to fall within the scope of the appended claims.

What is claimed is:

1. A process for the preparation of a compound of the Formula [II]

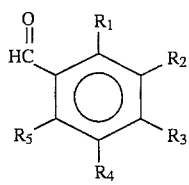

comprising contacting an aromatic compound of the Formula [I]

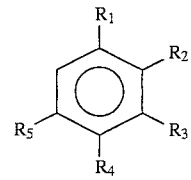

with a halogenated compound selected from the group consisting of

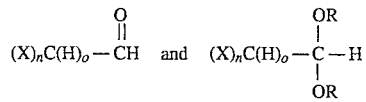

in the presence of a Lewis acid, followed by a base, wherein:

X is Cl, F or Br;

each R, independently, is H, or a $C_1$–$C_{30}$ alkyl which may be substituted with no more than one of the following groups: hydroxy, methoxy, ether, nitrile or nitro;

n is 2 or 3;

o is 3–n;

$R_1$ is a $C_1$–$C_{30}$ alkyl, or a $C_1$–$C_{30}$ alkoxy;

$R_2$ is H, a $C_1$–$C_{30}$ alkyl, or a $C_1$–$C_{30}$ alkoxy;

or $R_1$ and $R_2$ are taken together to form a $C_3$–$C_4$ alkyl, which may be substituted with one or more $C_1$–$C_{30}$ alkyl groups;

$R_3$ is H, a $C_1$–$C_{30}$ alkyl, or a $C_1$–$C_{30}$ alkoxy;

or $R_2$ and $R_3$ are taken together to form a $C_3$–$C_4$ alkyl, which may be substituted with one or more $C_1$–$C_{30}$ alkyl groups;

$R_4$ is H, a $C_1$–$C_{30}$ alkyl, or a $C_1$–$C_{30}$ alkoxy;

or $R_3$ and $R_1$ are taken together to form a $C_3$–$C_4$ alkyl, which may be substituted with one or more $C_1$–$C_{30}$ alkyl groups; and $R_5$ is a $C_1$–$C_{30}$ alkyl, or a $C_1$–$C_{30}$ alkoxy;

or $R_4$ and $R_5$ are taken together to form a $C_3$–$C_4$ alkyl, which may be substituted with one or more $C_1$–$C_{30}$ alkyl groups;

provided that:

(i) when $R_3$ is H, then $R_2$ and $R_4$ must be other than H;

(ii) no more than one of $R_1$, $R_2$, $R_3$, $R_4$ and $R_5$ are a $C_1$–$C_{30}$ alkoxy;

(iii) no more than two of $R_1$ and $R_2$, $R_2$ and $R_3$, $R_3$ and $R_4$, or $R_4$ and $R_5$, taken together, are a $C_3$–$C_4$ alkyl;

(iv) when $R_1$ and $R_2$, taken together, are a $C_3$–$C_4$ alkyl, then $R_2$ and $R_3$, may not be taken together to form a $C_3C_4$ alkyl;

(v) when $R_2$ and $R_3$, taken together, are a $C_3$–$C_4$ alkyl, then $R_3$ and $R_1$, may not be taken together to form a $C_3C_4$ alkyl;

(vi) when $R_3$ and $R_4$, taken together, are a $C_3$–$C_4$ alkyl, then $R_4$ and $R_5$, may not be taken together to form a $C_3C_4$ alkyl; and (vii) each $R_1$ and $R_2$, $R_2$ and $R_3$, $R_3$ and $R_4$, or $R_4$ and $R_5$ taken together to form a $C_4$ alkyl is substituted with no more than six $C_1$–$C_{30}$ alkyl groups.

2. A process of claim 1 wherein X is Cl or F.

3. A process of claim 1 wherein X is Cl.

4. A process of claim 1 wherein the halogenated compound is

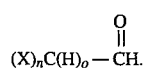

5. A process of claim 1 wherein the halogenated compound is

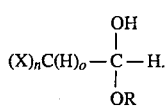

6. A process of claim 1 wherein the halogenated compound is

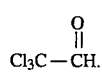

7. A process of claim 1 wherein the halogenated compound is

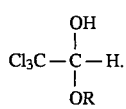

8. A process of claim 7 wherein R is a $C_4$–$C_{12}$ alkyl.

9. A process of claim 7 wherein R is selected from the group consisting of H, methyl, ethyl, propyl, n-butyl, iso-butyl, pentyl, n-pentyl, hexyl, iso-heptyl, 1-octyl, 2-octyl, iso-octyl, iso-nonyl, iso-decyl, dodecyl, tridecyl, iso-tridecyl, iso-hexadecyl, iso-octadecyl, 2- ethyl-1-hexyl, 2-methyl-butyl, 2-methyl-1-butyl, 3-methyl-2-butyl, 3-methyl-butyl, 3-methyl-1-butyl, 2-methyl-1-propyl, 3,7-dimethyloctyl, 2-methyl-pentyl, 2-ethyl-butyl, 2,3-dimethyl-butyl, 2-ethyl-hexyl, 2,4,4-trimethyl-1-pentyl, 3,5,5-trimethylhexyl, 3,5,5-trimethyl-1-hexyl, methoxyethyl, ethylene glycol, and mixtures thereof.

10. A process of claim 9 wherein R is selected from the group consisting of 2-ethyl-1-hexyl, 3-methyl-1-butyl, 2-methyl-1-butyl and 2-methyl-1-propyl.

11. A process of claim 10 wherein R is selected from the group consisting of 3-methyl-1-butyl and 2-methyl-1-butyl.

12. A process of claim 1 wherein:

$R_1$ is a $C_1$–$C_{10}$ alkyl;

$R_2$ is H or a $C_1$–$C_{10}$ alkyl;

or $R_1$ and $R_2$, taken together, are a $C_3$–$C_4$ alkyl which may be substituted with one or more $C_1$–$C_{10}$ alkyl groups;

$R_3$ is H or a $C_1$–$C_{10}$ alkyl;

or $R_2$ and $R_3$, taken together, are a $C_3$–$C_4$ alkyl which may be substituted with one or more $C_1$–$C_{10}$ alkyl groups;

$R_4$ is H or a $C_1$–$C_{10}$ alkyl;

or $R_3$ and $R_4$, taken together, are a $C_3$–$C_4$ alkyl which may be substituted with one or more $C_1$–$C_{10}$ alkyl groups; and $R_5$ is a $C_1$–$C_{10}$ alkyl;

or $R_4$ and $R_5$, taken together, are a $C_3$–$C_4$ alkyl which may be substituted with one or more $C_1$–$C_{10}$ alkyl groups.

13. A process of claim 12 wherein:

$R_1$ is a $C_1$–$C_3$ alkyl;

$R_2$ is H or a $C_1$–$C_3$ alkyl;

or $R_1$ and $R_2$, taken together, are a $C_3$–$C_4$ alkyl which may be substituted with one or more $C_1$–$C_3$ alkyl groups;

$R_3$ is H or a $C_1$–$C_3$ alkyl;

or $R_2$ and $R_3$, taken together, are a $C_3$–$C_4$ alkyl which may be substituted with one or more $C_1$–$C_3$ alkyl groups;

$R_4$ is H or a $C_1$–$C_3$ alkyl;

or $R_3$ and $R_4$, taken together, are a $C_3$–$C_4$ alkyl which may be substituted with one or more $C_1$–$C_3$ alkyl groups; and $R_5$ is a $C_1$–$C_3$ alkyl;

or $R_4$ and $R_5$, taken together, are a $C_3$–$C_4$ alkyl which may be substituted with one or more $C_1$–$C_3$ alkyl groups.

14. A process of claim 13 wherein:

$R_1$ and $R_2$, taken together, are a $C_3$–$C_4$ alkyl which may be substituted with one or more $C_1$–$C_3$ alkyl groups.

15. A process of claim 13 wherein:

$R_2$ and $R_3$, taken together, are a $C_3$–$C_4$ alkyl which may be substituted with one or more $C_1$–$C_3$ alkyl groups.

16. A process of claim 13 wherein:

$R_3$ and $R_4$, taken together, are a $C_3$–$C_4$ alkyl which may be substituted with one or more $C_1$–$C_3$ alkyl groups.

17. A process of claim 13 wherein:

$R_4$ and $R_5$, taken together, are a $C_3$–$C_4$ alkyl which may be substituted with one or more $C_1$–$C_3$ alkyl groups.

18. A process of claim 13 wherein:

$R_1$ is $CH_3$;

$R_2$ is H or $CH_3$;

or $R_1$ and $R_2$, taken together, are a $C_3$–$C_4$ alkyl which may be substituted with one or more $C_1$–$C_3$ alkyl groups;

$R_3$ is H or $CH_3$;

or $R_2$ and $R_3$, taken together, are a $C_3$–$C_4$ alkyl which may be substituted with one or more $C_1$–$C_3$ alkyl groups;

$R_4$ is H or an $CH_3$;

or $R_3$ and $R_4$, taken together, are a $C_3$–$C_4$ alkyl which may be substituted with one or more $C_1$–$C_3$ alkyl groups; and $R_5$ is $CH_3$;

or $R_4$ and $R_5$, taken together, are a $C_3$–$C_4$ alkyl which may be unsubstituted or substituted with one or more $C_1$–$C_3$ alkyl groups.

19. A process of claim 1 wherein the compound of Formula [I] is

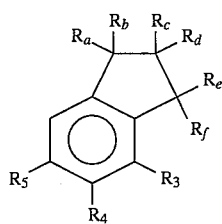

and the compound of Formula [II] is

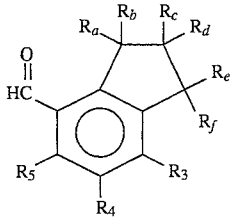

[IIa]

wherein:

$R_a$, $R_b$, $R_c$, $R_d$, $R_e$, $R_f$, $R_g$ and $R_h$ are, independently, H or a $C_1$–$C_{30}$ alkyl group.

20. A process of claim 1 wherein the compound of Formula [I] is

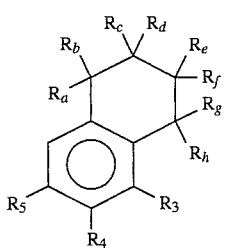

[Ib]

and the compound of Formula [II] is

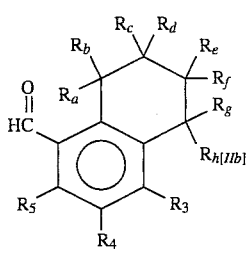

[IIb]

wherein:

$R_a$, $R_b$, $R_c$, $R_d$, $R_e$, $R_f$, $R_g$ and $R_h$ are, independently, H or a $C_1$–$C_{30}$ alkyl group.

21. A process of claim 1 wherein the compound of Formula [I] is

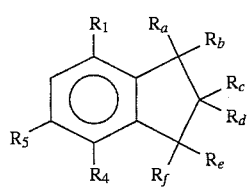

[Ic]

and the compound of Formula [II] is

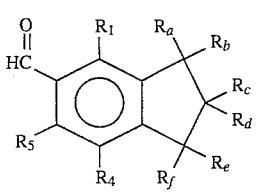

[IIc]

wherein:

$R_a$, $R_b$, $R_c$, $R_d$, $R_e$, $R_f$, $R_g$ and $R_h$ are, independently, H or a $C_1$–$C_{30}$ alkyl group.

22. A process of claim 21 wherein $R_1$ is $CH_3$, $R_4$ is H, $R_5$ is $CH_3$, $R_a$ is $CH_3$, $R_b$ is $CH_3$, $R_c$ is $CH_3$, $R_d$ is H, $R_e$ is $CH_3$, and $R_f$ is $CH_3$.

23. A process of claim 21 wherein $R_1$ is $CH_3$, $R_4$ is H, $R_5$ is $CH_3$, $R_a$ is $CH_3$, $R_b$ is $CH_2CH_3$, $R_c$ is H, $R_d$ is H, $R_e$ is $CH_3$, and $R_f$ is $CH_3$.

24. A process of claim 21 wherein $R_1$ is $CH_3$, $R_4$ is H, $R_5$ is $CH_3$, $R_a$ is $CH_3$, $R_b$ is $CH_3$, $R_c$ is H, $R_d$ is H, $R_e$ is $CH_3$, and $R_f$ is $CH_3$.

25. A process of claim 1 wherein the compound of Formula [I] is

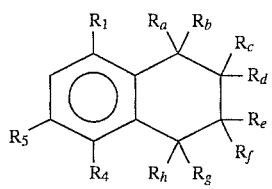

[Id]

and the compound of Formula [II] is

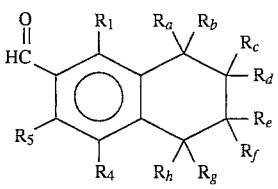

[IId]

wherein:

$R_a$, $R_b$, $R_c$, $R_d$, $R_e$, $R_f$, $R_g$ and $R_h$ are, independently, H or a $C_1$–$C_{30}$ alkyl group.

26. A process of claim 25 wherein $R_1$ is $CH_3$, $R_4$ is H, $R_5$ is $CH_3$, $R_a$ is $CH_3$, $R_b$ is $CH_3$, $R_c$ is H, $R_d$ is H, $R_e$ is $CH_3$, $R_f$ is H, $R_g$ is $CH_3$ and $R_h$ is $CH_3$.

27. A process of claim 25 wherein $R_1$ is $CH_3$, $R_4$ is H, $R_5$ is $CH_3$, $R_a$ is $CH_3$, $R_b$ is $CH_3$, $R_c$ is H, $R_d$ is H, $R_e$ is H, $R_f$ is H, $R_g$ is $CH_3$ and $R_h$ is $CH_3$.

28. A process of claim 1 wherein the compound of Formula [I] is

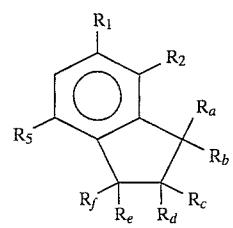

[Ie]

and the compound of Formula [II] is

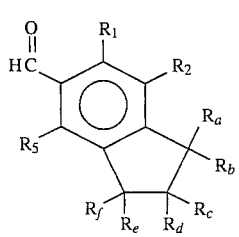

[IIe]

wherein:

$R_a$, $R_b$, $R_c$, $R_d$, $R_e$, $R_f$, $R_g$ and $R_h$ are, independently, H or a $C_1$–$C_{30}$ alkyl group.

29. A process of claim 1 wherein the compound of Formula [I] is

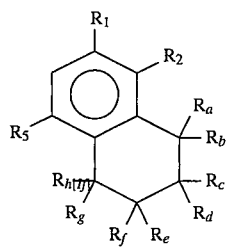

and the compound of Formula [II] is

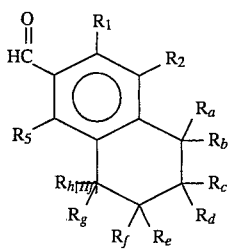

wherein:

$R_a$, $R_b$, $R_c$, $R_d$, $R_e$, $R_f$, $R_g$ and $R_h$ are, independently, H or a $C_1$–$C_{30}$ alkyl group.

30. A process of claim 1 wherein the compound of Formula [I] is

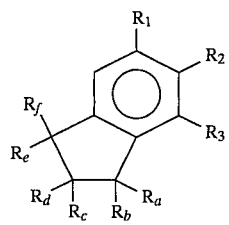

and the compound of Formula [II] is

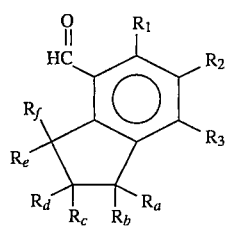

wherein:

$R_a$, $R_b$, $R_c$, $R_d$, $R_e$, $R_f$, $R_g$ and $R_h$ are, independently, H or a $C_1$–$C_{30}$ alkyl group.

31. A process of claim 1 wherein the compound of Formula [I] is

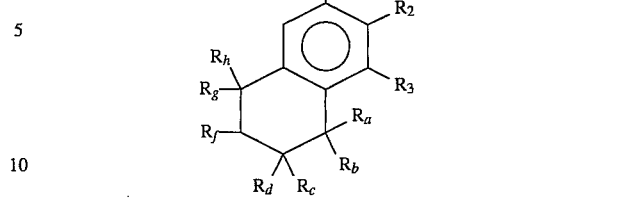

and the compound of Formula [II] is

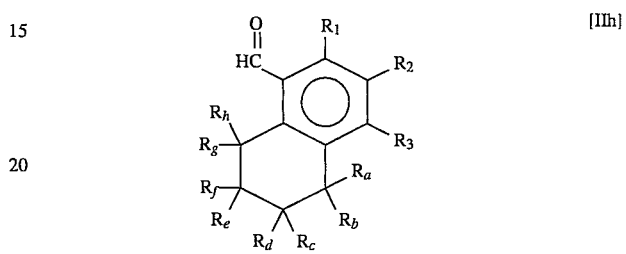

wherein:

$R_a$, $R_b$, $R_c$, $R_d$, $R_e$, $R_f$, $R_g$ and $R_h$ are, independently, H or a $C_1$–$C_{30}$ alkyl group.

32. A process of claim 1 wherein $R_3$ is $C_1$–$C_{30}$ alkyl.

33. A process of claim 1 wherein the compound of Formula [II] is 1,1,2,3,3,4,6-heptamethylindan-5-carboxaldehyde.

34. A process of claim 1 wherein the Lewis acid is a metal halide.

35. A process of claim 34 wherein the metal halide is selected from the group consisting of titanium chloride, aluminum chloride, aluminum bromide, iron chloride, boron fluoride and tin chloride.

36. A process of claim 35 wherein the metal halide is selected from the group consisting of titanium chloride and aluminum chloride.

37. A process of claim 36 wherein the metal halide is titanium chloride.

38. A process of claim 1 wherein the base is an inorganic base.

39. A process of claim 38 wherein the base is NaOH.

40. A process of claim 1 wherein the base is an organic base.

41. A process of claim 1 wherein the reaction is carried out in the presence of an additional solvent.

42. A process of claim 41 wherein the solvent is an unhalogenated aliphatic, unhalogenated alicyclic or unhalogenated aromatic hydrocarbon solvent.

43. A process of claim 42 wherein the solvent is an unhalogenated aliphatic or unhalogenated alicyclic hydrocarbon solvent.

44. A process of claim 43 wherein the solvent is selected from the group consisting of n-hexane, 2,2,4-trimethylpentane and cyclohexane.

45. A process of claim 1 wherein the process is carried out under conditions which minimize the amount of protonic acid in solution.

46. A process of claim 45 wherein the process is carried out using at least one of the following conditions: low polarity solvent, refluxing solvent, vigorous stirring, inert gas sweep, or a vacuum.

47. A process of claim 46 wherein the process is carried out under a vacuum.

48. A process of claim 46 wherein the process is carried out using a vacuum assisted sweep.

49. A process of claim 46 wherein the process is carried out using a refluxing solvent with a vacuum assist.

50. A process of claim 1 wherein the process is carried out at a temperature of between about −35° C. and about 25° C.

51. A process of claim 50 wherein the temperature is between about −20° C. and about 5° C.

52. A process of claim 51 wherein the temperature is between about −15° C. and about 0° C.

53. A product produced by the process of claim 1.

54. A product produced by the process of claim 45.

* * * * *

UNITED STATES PATENT AND TRADEMARK OFFICE
CERTIFICATE OF CORRECTION

PATENT NO. : 5,457,239  Page 1 of 6
DATED : October 10, 1995
INVENTOR(S) : Frank et al.

It is certified that error appears in the above-indentified patent and that said Letters Patent is hereby corrected as shown below:

In column 3, lines 51-52, please delete "to the conditions of the present process, wherein, in the above formulas, $R_1$ through $R_5$ are defined as follows:" and insert --to the conditions of the present process, wherein, in the above formulas, $R_1$ through $R_5$ are defined as follows:-- therefor.

In column 5, lines 50-58, please delete

" 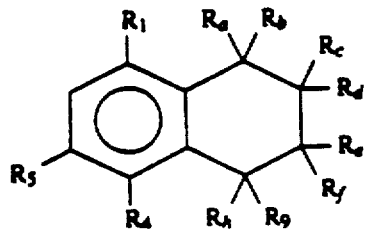 " and insert -- 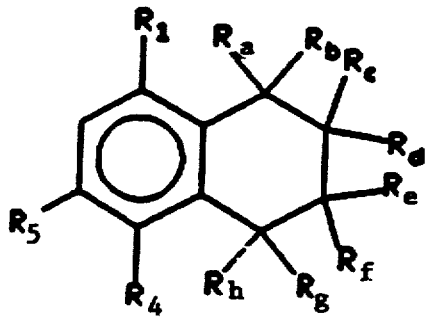 -- therefor.

UNITED STATES PATENT AND TRADEMARK OFFICE
CERTIFICATE OF CORRECTION

PATENT NO. : 5,457,239
DATED : October 10, 1995
INVENTOR(S) : Frank et al.

It is certified that error appears in the above-indentified patent and that said Letters Patent is hereby corrected as shown below:

In column 6, lines 4-10, please delete

" 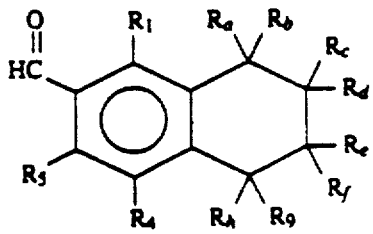 " and insert -- 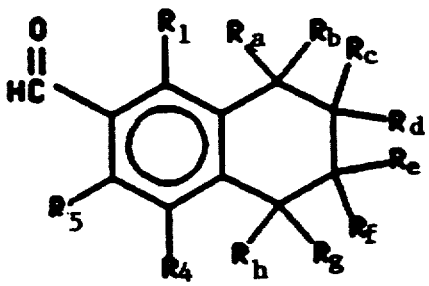 -- therefor.

UNITED STATES PATENT AND TRADEMARK OFFICE
CERTIFICATE OF CORRECTION

PATENT NO. : 5,457,239
DATED : October 10, 1995
INVENTOR(S) : Frank et al.

It is certified that error appears in the above-indentified patent and that said Letters Patent is hereby corrected as shown below:

In column 6, line 35, please delete "$R_a$ is $CH_3$, $R_5$" and insert --$R_5$ is $Ch_3$, $R_a$-- therefor.

In column 11, line 54, please delete "2-ethylbutyl" and insert --2-ethyl-butyl-- therefor.

In column 12, line 2, please delete "3-methyll" and insert --3-methyl-1-- therefor.

In column 17, line 6, please delete "from" and insert --form-- therefor.

In column 17, line 31, please delete "100° C. hold" and insert --100° C., hold-- therefor.

In column 17, line 34, please delete "235° C. and" and insert --235° C., and-- therefor.

In column 22, line 26, please delete "3-n" and insert --3 - n-- therefor.

In column 22, line 38, please delete "$R_1$" and insert --$R_4$-- therefor.

In column 22, line 55, please delete "$C_3C_4$" and insert --$C_3$-$C_4$-- therefor.

UNITED STATES PATENT AND TRADEMARK OFFICE
CERTIFICATE OF CORRECTION

PATENT NO. : 5,457,239
DATED : October 10, 1995
INVENTOR(S) : Frank et al.

It is certified that error appears in the above-indentified patent and that said Letters Patent is hereby corrected as shown below:

In column 22, line 57, please delete "$R_1$" and insert --$R_4$-- therefor.

In column 22, line 58, please delete "$C_3C_4$" and insert --$C_3$-$C_4$-- therefor.

In column 22, line 61, please delete "$C_3C_4$" and insert --$C_3$-$C_4$-- therefor.

In column 25, line 35, please delete "Rh[IIb]" and insert --Rh-- therefor.

In column 25, line 35, at the end of the line, please insert --[IIb]--.

In column 27, line 9, please delete "Rh[If]" and insert --Rh-- therefor.

In column 27, line 9, at the end of the line, please insert --[If]--.

In column 27, line 22, please delete "Rh[IIf]" and insert --Rh-- therefor.

In column 27, line 22, at the end of the line, please insert --[IIf]--.

UNITED STATES PATENT AND TRADEMARK OFFICE
CERTIFICATE OF CORRECTION

PATENT NO. : 5,457,239
DATED : October 10, 1995
INVENTOR(S) : Frank et al.

It is certified that error appears in the above-indentified patent and that said Letters Patent is hereby corrected as shown below:

In column 28, lines 1-10, please delete

" 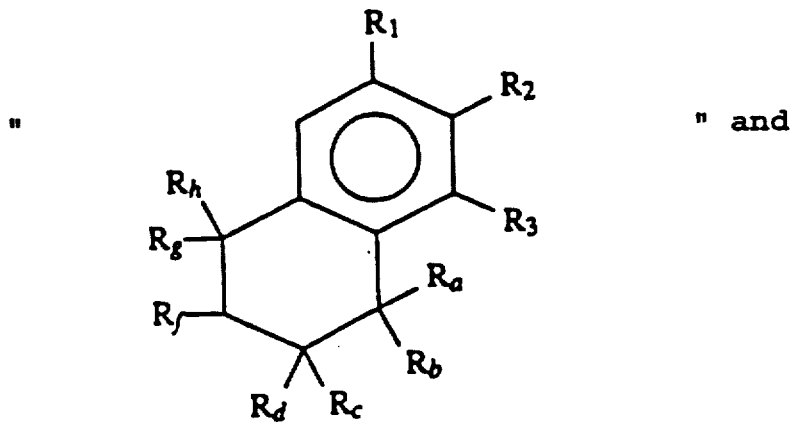 " and

UNITED STATES PATENT AND TRADEMARK OFFICE
CERTIFICATE OF CORRECTION

PATENT NO. : 5,457,239
DATED : October 10, 1995
INVENTOR(S) : Frank et al

It is certified that error appears in the above-indentified patent and that said Letters Patent is hereby corrected as shown below:

insert -- 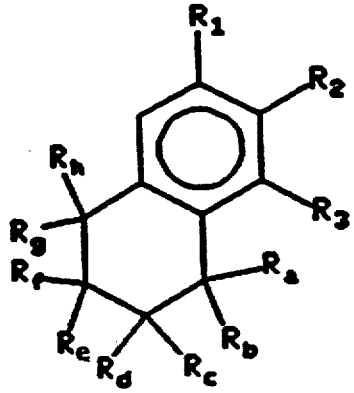 -- therefor.

Signed and Sealed this

Twenty-third Day of April, 1996

Attest:

BRUCE LEHMAN

Attesting Officer

Commissioner of Patents and Trademarks